(12) United States Patent
Margoles et al.

(10) Patent No.: US 9,860,687 B2
(45) Date of Patent: Jan. 2, 2018

(54) BUILDING SENSOR ARRAY

(71) Applicants: Ryan Margoles, Denver, CO (US);
Brett Jurgens, Denver, CO (US)

(72) Inventors: Ryan Margoles, Denver, CO (US);
Brett Jurgens, Denver, CO (US)

(73) Assignee: Loop Labs, Inc., Denver, CO (US)

( * ) Notice: Subject to any disclaimer, the term of this patent is extended or adjusted under 35 U.S.C. 154(b) by 159 days.

(21) Appl. No.: 14/675,174

(22) Filed: Mar. 31, 2015

(65) Prior Publication Data

US 2015/0281883 A1    Oct. 1, 2015

Related U.S. Application Data

(60) Provisional application No. 61/973,020, filed on Mar. 31, 2014, provisional application No. 62/054,387, filed on Sep. 24, 2014.

(51) Int. Cl.
*G01N 29/12* (2006.01)
*H04W 4/02* (2009.01)

(52) U.S. Cl.
CPC .................................. *H04W 4/02* (2013.01)

(58) Field of Classification Search
CPC .................................................. G01N 29/12
See application file for complete search history.

(56) References Cited

U.S. PATENT DOCUMENTS

| | | | | |
|---|---|---|---|---|
| 3,438,493 A | * | 4/1969 | Goble | G01N 29/04 209/590 |
| 4,745,398 A | * | 5/1988 | Abel | G08B 23/00 340/500 |
| 7,466,224 B2 | * | 12/2008 | Ward | G07C 9/00111 340/5.2 |
| 2010/0089160 A1 | * | 4/2010 | Cosentino | G01L 1/255 73/579 |

FOREIGN PATENT DOCUMENTS

RU    2544745 C1 * 3/2015

* cited by examiner

*Primary Examiner* — Robert R Raevis
(74) *Attorney, Agent, or Firm* — Kilpatrick Townsend & Stockton LLP

(57) ABSTRACT

A method for determining the locations of sensor devices in a sensor array in a structure is disclosed. The method may include placing a sensor device at a location. The method may also include receiving, at a mobile device, an identifier of the sensor device. The method may further include determining, by the mobile device, a compass direction and elevation angle from the sensor device to a base station. The method may additionally include determining a distance between the sensor device and the base station. The method may moreover include determining a location of the sensor device based at least in part on the compass direction and the elevation angle from the sensor device to the base station, and the distance between the sensor device and the base station. The method may furthermore include storing the location of the sensor in association with the identifier of the sensor device.

5 Claims, 4 Drawing Sheets

BUILDING SENSOR ARRAY

CROSS-REFERENCE TO RELATED APPLICATIONS

This application claims priority to Provisional U.S. Patent Application No. 61/973,020 filed Mar. 31, 2014, entitled "D-TECHT AWARENESS PLATFORM" and Provisional U.S. Patent Application No. 62/054,387 filed Sep. 24, 2014, entitled "MONITORING OF FULLNESS OF A CLOSED SYSTEM USING A PIEZOELECTRIC TRANSDUCER." The entire disclosures of both of the aforementioned Provisional U.S. patent applications are hereby incorporated by reference, for all purposes, as if fully set forth herein.

BACKGROUND OF THE INVENTION

This invention relates generally to sensors. More specifically the invention relates to building environmental sensors and arrays of such sensors.

BRIEF DESCRIPTION OF THE INVENTION

In one embodiment, a method for determining the locations of sensor devices in a sensor array in a structure is provided. The method may include placing a first sensor device at a first location. The method may also include receiving, at a mobile communication device, an identifier of the first sensor device. The method may further include determining, by the mobile communication device, a compass direction and elevation angle from the first sensor device to a base station. The method may additionally include determining a distance between the first sensor device and the base station. The method may moreover include determining a location of the first sensor device based at least in part on the compass direction and the elevation angle from the first sensor device to the base station, and the distance between the first sensor device and the base station. The method may furthermore include storing, in a database, the location of the first sensor in association with the identifier of the first sensor device.

In another embodiment, a method for sensing changes to a pane of glass is provided. The method may include disposing a piezoelectric transducer onto a surface of the pane of glass. The method may also include activating the piezoelectric transducer for a first period of time to generate a first vibration of the pane of glass. The method may further include converting, by the piezoelectric transducer, the first vibration of the pane of glass into a first electric signal. The method may additionally include analyzing, by a processor, the first electric signal to determine a first natural frequency of the pane of glass. The method may moreover include activating the piezoelectric transducer for a second period of time to generate a second vibration of the pane of glass. The method may furthermore include converting, by the piezoelectric transducer, the second vibration of the pane of glass into a second electric signal. The method may also include analyzing, by the processor, the second electric signal to determine a second natural frequency of the pane of glass. The method may further include determining, by the processor, the second natural frequency is different by at least a threshold amount from the first natural frequency. The method may additionally include, based at least in part on the second natural frequency being different by at least the threshold amount from the first natural frequency, determining, by the processor, that the physical characteristics of the pane of glass have changed between the first period of time and the second period of time.

In another embodiment, a method for sensing changes to a volume of fluid in a container is provided. The method may include disposing a piezoelectric transducer onto an outer surface of the container. The method may also include activating the piezoelectric transducer for a first period of time to generate a first vibration of the container. The method may further include converting, by the piezoelectric transducer, the first vibration of the container into a first electric signal. The method may additionally include analyzing, by a processor, the first electric signal to determine a first natural frequency of the container. The method may moreover include activating the piezoelectric transducer for a second period of time to generate a second vibration of the container. The method may furthermore include converting, by the piezoelectric transducer, the second vibration of the container into a second electric signal. The method may also include analyzing, by the processor, the second electric signal to determine a second natural frequency of the container. The method may further include determining, by the processor, the second natural frequency is different by at least a threshold amount from the first natural frequency. The method may additionally include, based at least in part on the second natural frequency being different by at least the threshold amount from the first natural frequency, determining, by the processor, that the volume of fluid in the container has changed between the first period of time and the second period of time.

BRIEF DESCRIPTION OF THE DRAWINGS

The present invention is described in conjunction with the appended figures.

Figure 1:
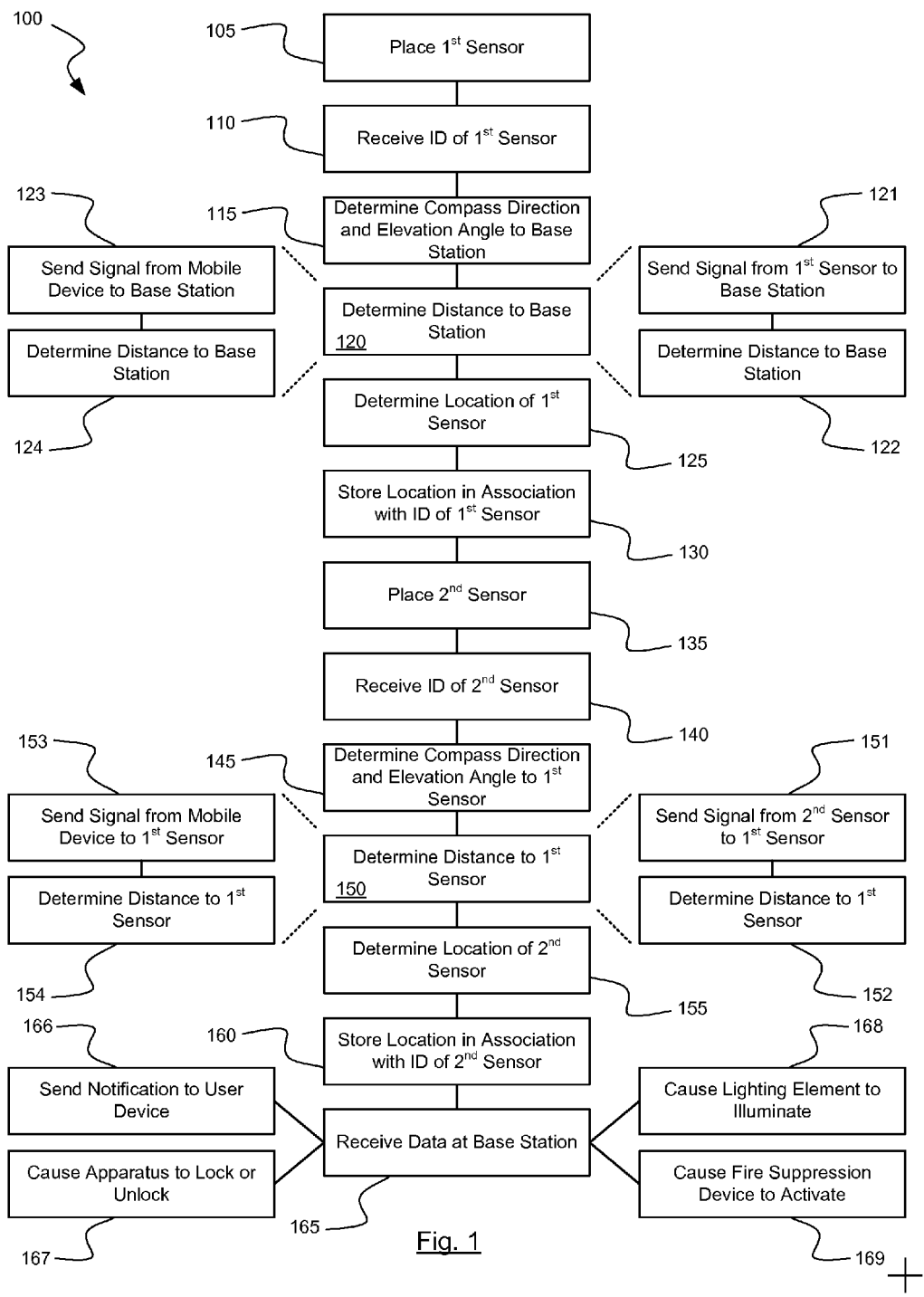
FIG. 1 is a block diagram of one embodiment of the invention for a method for determining the locations of sensor devices in a sensor array in a structure.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

In one embodiment of the invention, a method for determining the locations of sensor devices in a sensor array in a structure is provided. One such method 100 is shown in FIG. 1.

At block 105, the method may include placing a first sensor device at a first location. At block 110, the method may also include receiving, at a mobile communication device, an identifier of the first sensor device. At block 115, the method may further include determining, by the mobile communication device, a compass direction and elevation angle from the first sensor device to a base station.

At block 120, the method may additionally include determining a distance between the first sensor device and the base station. In some embodiments, determining a distance between the first sensor device and the base station may include, at block 121, sending a signal from the first sensor device to the base station, and at block 122, determining a distance between the first sensor device and the base station based at least in part on the signal. In other embodiments, determining a distance between the first sensor device and the base station may include, at block 123, sending a signal from the mobile communication device to the base station, and at block 124, determining a distance between the mobile communication device and the base station based at least in part on the signal.

At block 125, the method may moreover include determining a location of the first sensor device based at least in part on the compass direction and the elevation angle from the first sensor device to the base station, and the distance between the first sensor device and the base station. At block 130, the method may furthermore include storing, in a database, the location of the first sensor in association with the identifier of the first sensor device.

At block 135 the method may include placing a second sensor device at a second location. At block 140, the method may also include receiving, at the mobile communication device, an identifier of the second sensor device. At block 145, the method may further include determining, by the mobile communication device, a compass direction and elevation angle from the second sensor device to the first sensor device.

At block 150, the method may additionally include determining a distance between the second sensor device and the first sensor device. In some embodiments, determining a distance between the second sensor device and the first sensor device may include, at block 151, sending a signal from the second sensor device to the first sensor device, and at block 152, determining a distance between the second sensor device and the first sensor device based at least in part on the signal. In other embodiments, determining a distance between the second sensor device and the first sensor device may include, at block 153, sending a signal from the mobile communication device to the first sensor device, and at block 154, determining a distance between the mobile communication device and the first sensor device based at least in part on the signal.

At block 155, the method may moreover include determining a location of the second sensor device based at least in part on the compass direction and the elevation angle from the second sensor device to the first sensor device, the distance between the second sensor device and the first sensor device, and the location of the first sensor. At block 160, the method may furthermore include storing, in the database, the location of the second sensor in association with the identifier of the second sensor device.

At block 165, the method may include receiving data at the base station, from at least one of the first sensor device or the second sensor device. At block 166, based at least in part on the data, the method may include sending a notification to a user device thereby alerting a user of the user device. At block 167, based at least in part on the data, the method may also include causing an apparatus to unlock. At block 168, based at least in part on the data, the method may further include causing a lighting element to illuminate an exit path from the structure. At block 169, based at least in part on the data, the method may additionally include causing a fire suppression device to activate.

Figure 2:
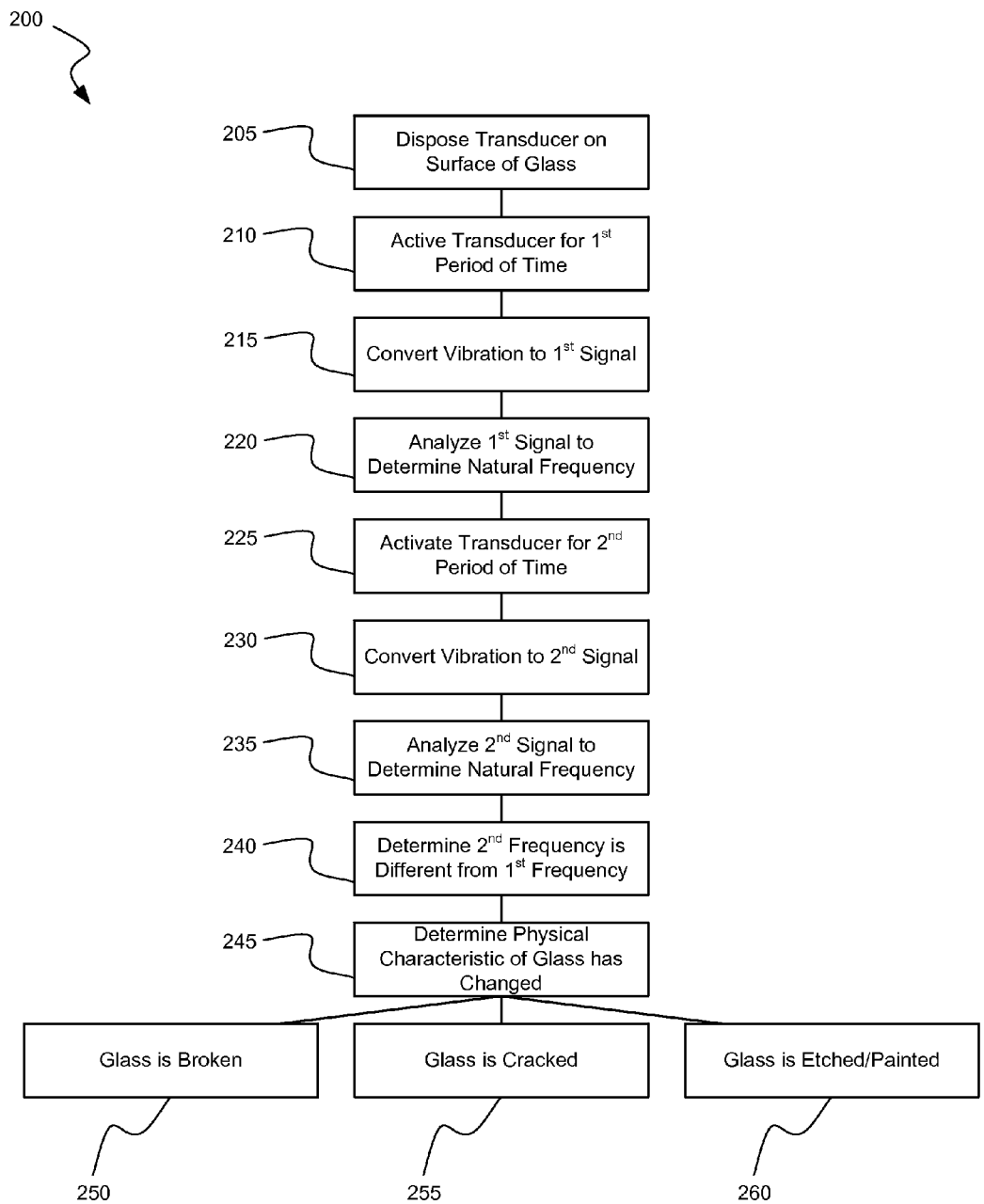
FIG. 2 is a block diagram of another embodiment of the invention for a method for sensing changes to a pane of glass.

In another embodiment of the invention, a method for sensing changes to a pane of glass is provided. One such method is shown in FIG. 2.

At block 205, the method may include disposing a piezoelectric transducer onto a surface of the pane of glass. At block 210, the method may also include activating the piezoelectric transducer for a first period of time to generate a first vibration of the pane of glass. At block 215, the method may further include converting, by the piezoelectric transducer, the first vibration of the pane of glass into a first electric signal. At block 220, the method may additionally include analyzing, by a processor, the first electric signal to determine a first natural frequency of the pane of glass.

At block 225, the method may moreover include activating the piezoelectric transducer for a second period of time to generate a second vibration of the pane of glass. At block 230, the method may furthermore include converting, by the piezoelectric transducer, the second vibration of the pane of glass into a second electric signal. At block 235, the method may also include analyzing, by the processor, the second electric signal to determine a second natural frequency of the pane of glass. At block 240, the method may further include determining, by the processor, the second natural frequency is different by at least a threshold amount from the first natural frequency.

At block 245, the method may additionally include, based at least in part on the second natural frequency being different by at least the threshold amount from the first natural frequency, determining, by the processor that the physical characteristics of the pane of glass have changed between the first period of time and the second period of time. This may include determining at block 250 that the glass is broken, determining at block 255 that the glass is cracked, or determining at block 260 that the glass is etched/painted.

Figure 3:
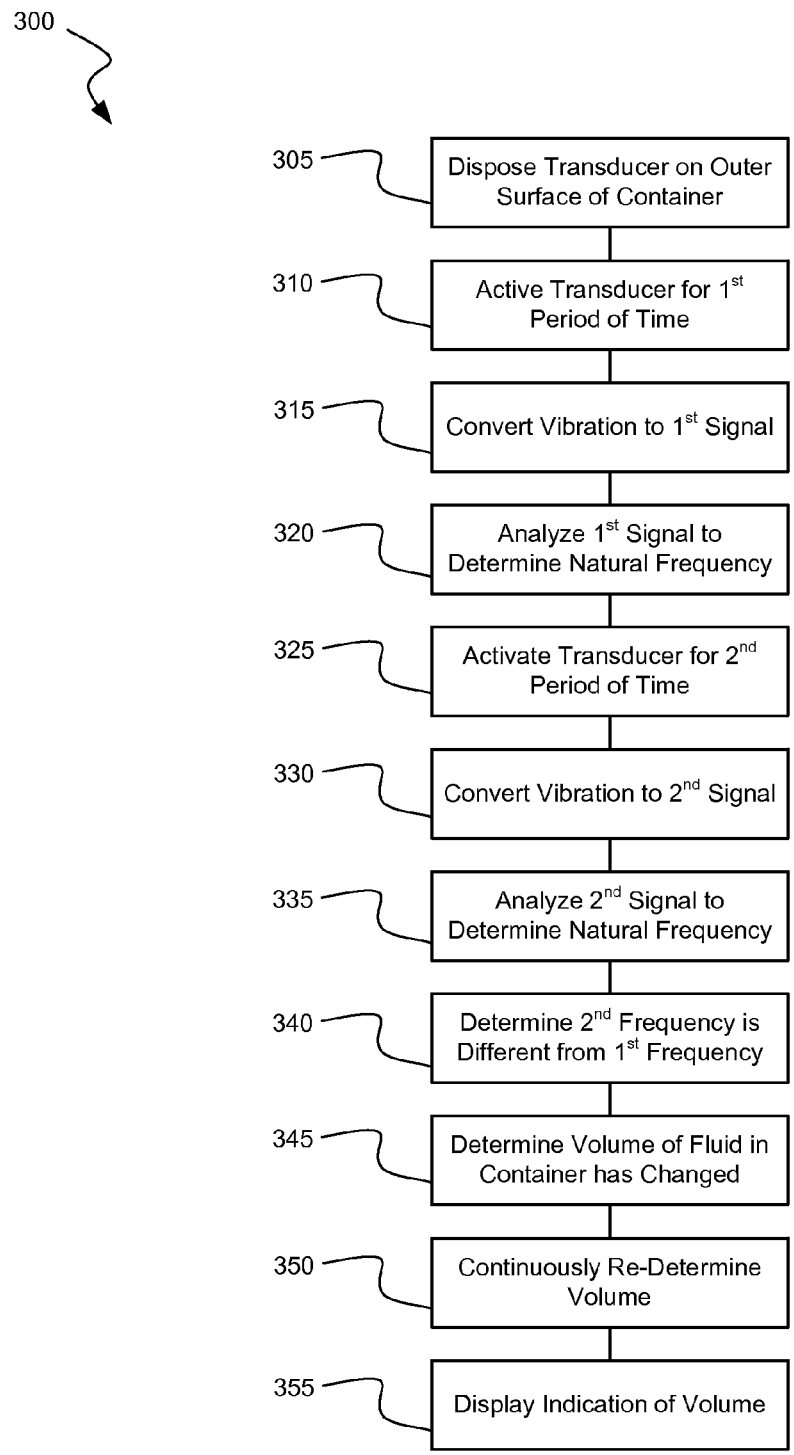
FIG. 3 is a block diagram of another embodiment of the invention for a method for sensing changes to a volume of fluid in a container.

In another embodiment of the invention, a method for sensing changes to a volume of fluid in a container is provided. One such method is shown in FIG. 3. The container may be a single walled vessel, a fuel/gas tank, a keg, and/or other vessel.

At block 305, the method may include disposing a piezoelectric transducer onto an outer surface of the container. At block 310, the method may also include activating the piezoelectric transducer for a first period of time to generate a first vibration of the container. At block 315, the method may further include converting, by the piezoelectric transducer, the first vibration of the container into a first electric signal. At block 320, the method may additionally include analyzing, by a processor, the first electric signal to determine a first natural frequency of the container.

At block 325, the method may moreover include activating the piezoelectric transducer for a second period of time to generate a second vibration of the container. At block 330, the method may furthermore include converting, by the piezoelectric transducer, the second vibration of the container into a second electric signal. At block 335, the method may also include analyzing, by the processor, the second electric signal to determine a second natural frequency of the container. At block 340, the method may further include determining, by the processor, the second natural frequency is different by at least a threshold amount from the first natural frequency.

At block 345, the method may additionally include, based at least in part on the second natural frequency being different by at least the threshold amount from the first natural frequency, determining, by the processor, that the volume of fluid in the container has changed between the first period of time and the second period of time. At block 350, the method may include continuously re-determining, by the processor, the volume of the fluid in the container. At block 355, the method may also include causing, by the processor, an indication of the volume of fluid in the container to be displayed to a user.

Figure 4:
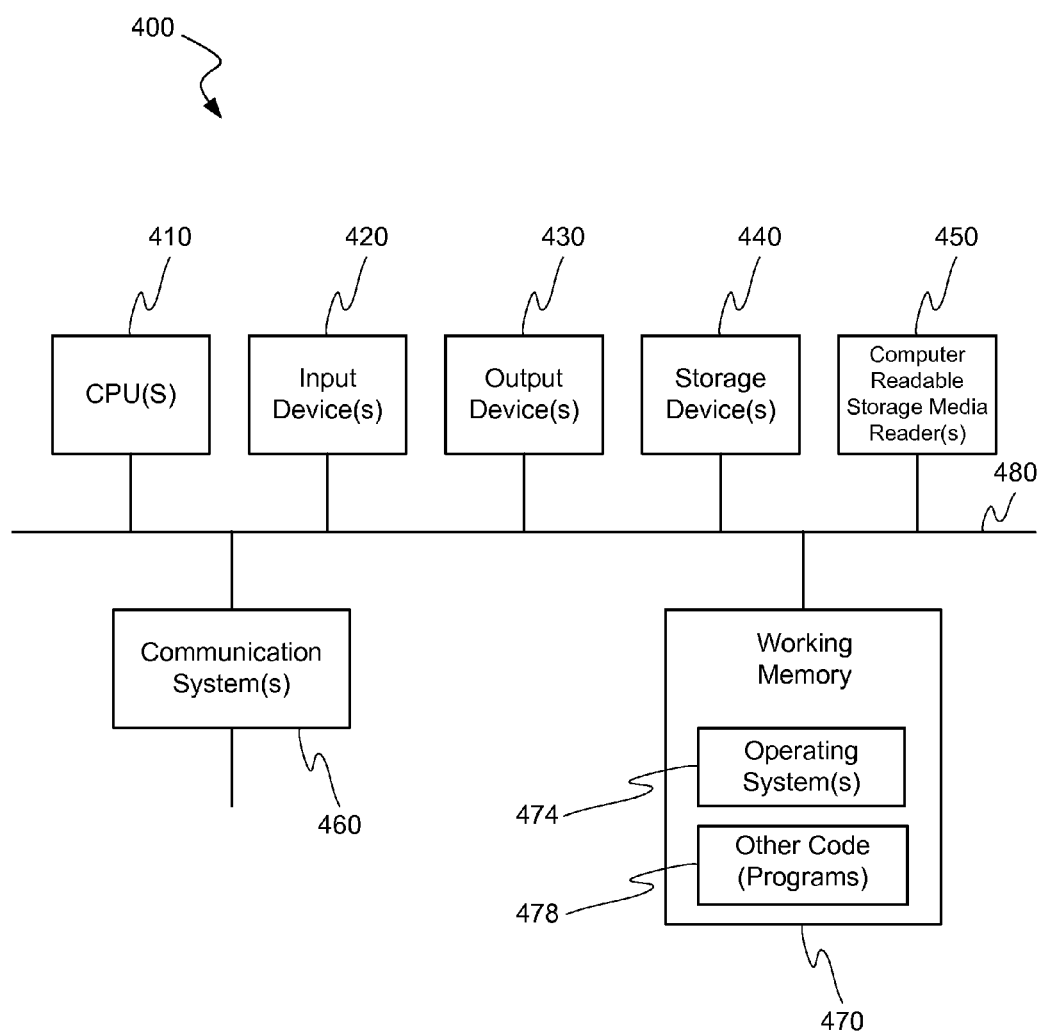
FIG. 4 is a block diagram of an exemplary computer system capable of being used in at least some portion of the apparatuses or systems of the present invention, or implementing at least some portion of the methods of the present invention.

FIG. 4 is a block diagram illustrating an exemplary computer system 400 in which embodiments of the present invention may be implemented. This example illustrates a computer system 400 such as may be used, in whole, in part, or with various modifications, to provide the functions of the sensor devices, the base station, the mobile communication device, the processor, the piezoelectric transducer, and/or other components of the invention such as those discussed above. For example, various functions of the processor may be controlled by the computer system 400, including, merely by way of example, analyzing electric signals to determine natural frequencies, determining volume or physical changes, etc.

The computer system 400 is shown comprising hardware elements that may be electrically coupled via a bus 490. The hardware elements may include one or more central processing units 410, one or more input devices 420 (e.g., a mouse, a keyboard, etc.), and one or more output devices 430 (e.g., a display device, a printer, etc.). The computer system 400 may also include one or more storage device 440. By way of example, storage device(s) 440 may be disk drives, optical storage devices, solid-state storage device such as a random access memory ("RAM") and/or a read-only memory ("ROM"), which can be programmable, flash-updateable and/or the like.

The computer system 400 may additionally include a computer-readable storage media reader 450, a communications system 460 (e.g., a modem, a network card (wireless or wired), an infra-red communication device, Bluetooth™ device, cellular communication device, etc.), and working memory 480, which may include RAM and ROM devices as described above. In some embodiments, the computer system 400 may also include a processing acceleration unit 470, which can include a digital signal processor, a special-purpose processor and/or the like.

The computer-readable storage media reader 450 can further be connected to a computer-readable storage medium, together (and, optionally, in combination with storage device(s) 440) comprehensively representing remote, local, fixed, and/or removable storage devices plus storage media for temporarily and/or more permanently containing computer-readable information. The communications system 460 may permit data to be exchanged with a network, system, computer and/or other component described above.

The computer system 400 may also comprise software elements, shown as being currently located within a working memory 480, including an operating system 484 and/or other code 488. It should be appreciated that alternate embodiments of a computer system 400 may have numerous variations from that described above. For example, customized hardware might also be used and/or particular elements might be implemented in hardware, software (including portable software, such as applets), or both. Furthermore, connection to other computing devices such as network input/output and data acquisition devices may also Occur.

Software of computer system 400 may include code 488 for implementing any or all of the function of the various elements of the architecture as described herein. For example, software, stored on and/or executed by a computer system such as system 400, can provide the functions of the sensor devices, the base station, the mobile communication device, the processor, the piezoelectric transducer, and/or other components of the invention such as those discussed above. Methods implementable by software on some of these components have been discussed above in more detail.

The invention has now been described in detail for the purposes of clarity and understanding. However, it will be appreciated that certain changes and modifications may be practiced within the scope of the appended claims.

What is claimed is:

1. A method for sensing changes to a pane of glass, wherein the method comprises:
   disposing a piezoelectric transducer onto a surface of the pane of glass;
   activating the piezoelectric transducer for a first period of time to generate a first vibration of the pane of glass;
   converting, by the piezoelectric transducer, the first vibration of the pane of glass into a first electric signal;
   analyzing, by a processor, the first electric signal to determine a first natural frequency of the pane of glass;
   activating the piezoelectric transducer for a second period of time to generate a second vibration of the pane of glass;
   converting, by the piezoelectric transducer, the second vibration of the pane of glass into a second electric signal;
   analyzing, by the processor, the second electric signal to determine a second natural frequency of the pane of glass;
   determining, by the processor the second natural frequency is different by at least a threshold amount from the first natural frequency; and
   based at least in part on the second natural frequency being different by at least the threshold amount from the first natural frequency, determining, by the processor, that a physical characteristic of the pane of glass has changed between the first period of time and the second period of time.

2. The method for sensing changes to a pane of glass of claim 1, wherein determining, by the processor, that the physical characteristic of the pane of glass has changed comprises:
   determining, by the processor, based on a difference between the second natural frequency and the first natural frequency, that the pane of glass is broken.

3. The method for sensing changes to a pane of glass of claim 1, wherein determining, by the processor, that the physical characteristic of the pane of glass has changed comprises:
   determining, by the processor, based on a difference between the second natural frequency and the first natural frequency, that the pane of glass is cracked.

4. The method for sensing changes to a pane of glass of claim 1, wherein determining, by the processor, that the physical characteristic of the pane of glass has changed comprises:
   determining, by the processor, based on a difference between the second natural frequency and the first natural frequency, that the pane of glass is etched.

5. The method for sensing changes to a pane of glass of claim 4, wherein the pane of glass being etched comprises:
   the pane of glass being at least partially painted.

* * * * *